United States Patent
Navarrete et al.

(10) Patent No.: US 11,468,997 B2
(45) Date of Patent: Oct. 11, 2022

(54) METHODS FOR ESTIMATING INJURY RECOVERY TIME DATA AND DEVICES THEREOF

(71) Applicant: Mitchell International, Inc., San Diego, CA (US)

(72) Inventors: Jonathan Navarrete, San Diego, CA (US); Olaf Wied, San Diego, CA (US); Norman E. Tyrrell, San Diego, CA (US)

(73) Assignee: Mitchell International, Inc., San Diego, CA (US)

( * ) Notice: Subject to any disclaimer, the term of this patent is extended or adjusted under 35 U.S.C. 154(b) by 339 days.

(21) Appl. No.: 16/788,540

(22) Filed: Feb. 12, 2020

(65) Prior Publication Data

US 2020/0258638 A1 Aug. 13, 2020

Related U.S. Application Data

(60) Provisional application No. 62/804,282, filed on Feb. 12, 2019.

(51) Int. Cl.
*G06Q 40/00* (2012.01)
*G16H 50/50* (2018.01)
(Continued)

(52) U.S. Cl.
CPC ............. *G16H 50/50* (2018.01); *G16H 10/60* (2018.01); *G16H 20/10* (2018.01)

(58) Field of Classification Search
CPC ........ G06Q 40/00; G06Q 40/08; G06H 50/50; G06H 10/60; G06H 20/10
See application file for complete search history.

(56) References Cited

U.S. PATENT DOCUMENTS

| 10,166,019 B2 * | 1/2019 | Nawana | ............. A61B 5/4848 |
| 2011/0112853 A1 * | 5/2011 | Tong | ..................... G16H 70/60 705/2 |

(Continued)

FOREIGN PATENT DOCUMENTS

IN 202211015617 A * 4/2022

OTHER PUBLICATIONS

Analysis of Injuries and Costs of Public Safety Occupations: a Systematic Review J Witmer—2019—digitalcommons.winthrop.edu (Year: 2019).*

*Primary Examiner* — Lalita M Hamilton

(57) ABSTRACT

Disclosed technology includes extracting claimant medical data including a current claimant's age, gender, and at least one injury from an electronic claims document. Estimated injury recovery time data is determined by correlating demographic medical data comprising prior estimated injury recovery time data associated with different prior claimant's ages, genders, and injuries based on programmed estimation rules configured to identify statistical correspondence between different combinations of the ages, the genders, and the injuries in the demographic medical data and the claimant medical data comprising at least the current claimant's age, gender, and at least one injury. The determined estimated injury recovery time data is updated based on at least identified and obtained medical treatment data and prescription medication data associated with the current claimant's at least one injury. The updated estimated injury recovery time data is provided via a graphical user interface to a claim management device.

18 Claims, 4 Drawing Sheets

(51) Int. Cl.
*G16H 20/10* (2018.01)
*G16H 10/60* (2018.01)

(56) References Cited

U.S. PATENT DOCUMENTS

| 2014/0081659 | A1* | 3/2014 | Nawana | A61B 5/4833 |
| | | | | 705/3 |
| 2022/0013217 | A1* | 1/2022 | Vogel | G16H 20/30 |

* cited by examiner

METHODS FOR ESTIMATING INJURY RECOVERY TIME DATA AND DEVICES THEREOF

This application claims the benefit of U.S. Provisional Patent Application Ser. No. 62/804,282, filed Feb. 12, 2019, which is hereby incorporated by reference in its entirety.

FIELD

This technology generally relates to methods for accurately estimating injury recovery time data and devices thereof.

BACKGROUND

Estimation of an expected recovery date of a claimant has always been very challenging and difficult because of the large number of variables which can impact the accuracy of any estimation. In particular, estimation of recovery time is impacted by correctly identifying and obtaining the correct data on which to base an estimate and then also properly analyzing the identified and obtained data. Unfortunately, to date this estimation of recovery time has been fraught with errors and inconsistencies impacting many downstream processes that rely on this determination.

To date prior software estimation tools to assist with estimating recovery time have had very limited capabilities. Many simply provide graphical user interfaces which enable the input and organization of data, but do not address the technological problems associated with correctly identifying and obtaining the necessary data to determine a reliable and consistent estimated recovery time or with properly analyzing the identified and obtained data to determine the estimation. Additionally, prior software estimation tools have failed to consider whether any determined estimated expected recovery date is an outlier to assist with fraud detection in the electronic processing of insurance claims.

SUMMARY

A method for accurately estimating injury recovery time data comprising extracting claimant medical data including at least a current claimant's age, gender, and at least one injury from an electronic claims document. Estimated injury recovery time data is determined by correlating at least demographic medical data comprising prior estimated injury recovery time data associated with different prior claimant's ages, genders, and injuries based on one or more programmed estimation rules configured to identify statistical correspondence between different combinations of the ages, the genders, and the injuries in the demographic medical data and the claimant medical data comprising at least the current claimant's age, gender, and at least one injury. The determined estimated injury recovery time data is updated based on at least identified and obtained medical treatment data and prescription medication data associated with the current claimant's at least one injury. The updated estimated injury recovery time data is provided via a graphical user interface to a requesting claim management device.

A non-transitory computer readable medium having stored thereon instructions for accurately estimating injury recovery time data comprising executable code, which when executed by at least one processor, cause the processor to extract claimant medical data including at least a current claimant's age, gender, and at least one injury from an electronic claims document. Estimated injury recovery time data is determined by correlating at least demographic medical data comprising prior estimated injury recovery time data associated with different prior claimant's ages, genders, and injuries based on one or more programmed estimation rules configured to identify statistical correspondence between different combinations of the ages, the genders, and the injuries in the demographic medical data and the claimant medical data comprising at least the current claimant's age, gender, and at least one injury. The determined estimated injury recovery time data is updated based on at least identified and obtained medical treatment data and prescription medication data associated with the current claimant's at least one injury. The updated estimated injury recovery time data is provided via a graphical user interface to a requesting claim management device.

An injury recovery estimation computing apparatus includes a memory coupled to the processor which is configured to be capable of executing programmed instructions comprising and stored in the memory to extract claimant medical data including at least a current claimant's age, gender, and at least one injury from an electronic claims document. Estimated injury recovery time data is determined by correlating at least demographic medical data comprising prior estimated injury recovery time data associated with different prior claimant's ages, genders, and injuries based on one or more programmed estimation rules configured to identify statistical correspondence between different combinations of the ages, the genders, and the injuries in the demographic medical data and the claimant medical data comprising at least the current claimant's age, gender, and at least one injury. The determined estimated injury recovery time data is updated based on at least identified and obtained medical treatment data and prescription medication data associated with the current claimant's at least one injury. The updated estimated injury recovery time data is provided via a graphical user interface to a requesting claim management device.

Accordingly, this technology provides methods, non-transitory computer readable medium, and apparatuses that accurately estimating injury recovery time data. By using the techniques illustrated below, the disclosed technology provides a technological solution by considering large amounts of medical data associated with the claimant and the demographic data in different formats while estimating the injury recovery time. Additionally, the disclosed technology also identifies any possible outliers with respect to the amount of time taken to recover from an injury and sends out a notification for further investigation. By doing so, the disclosed technology is able to prevent fraudulent insurance claims from being processed and therefore is closely tied to the practical application of estimating injury recovery time.

DETAILED DESCRIPTION

An environment 10 with an example of an injury recovery estimation computing apparatus 14 is illustrated in FIGS.

1-2. In this particular example, the environment 10 includes the injury recovery estimation computing apparatus 14, a plurality of claims management devices 12(1)-12(n), plurality of medical data servers 13(1)-13(n), plurality of claimant data servers 16(1)-16(n) coupled via one or more communication networks 18, although the environment could include other types and numbers of systems, devices, components, and/or other elements as is generally known in the art and will not be illustrated or described herein. This technology provides a number of advantages including providing methods, non-transitory computer readable medium, and apparatuses that accurately predict injury recovery time data data.

Figure 1:
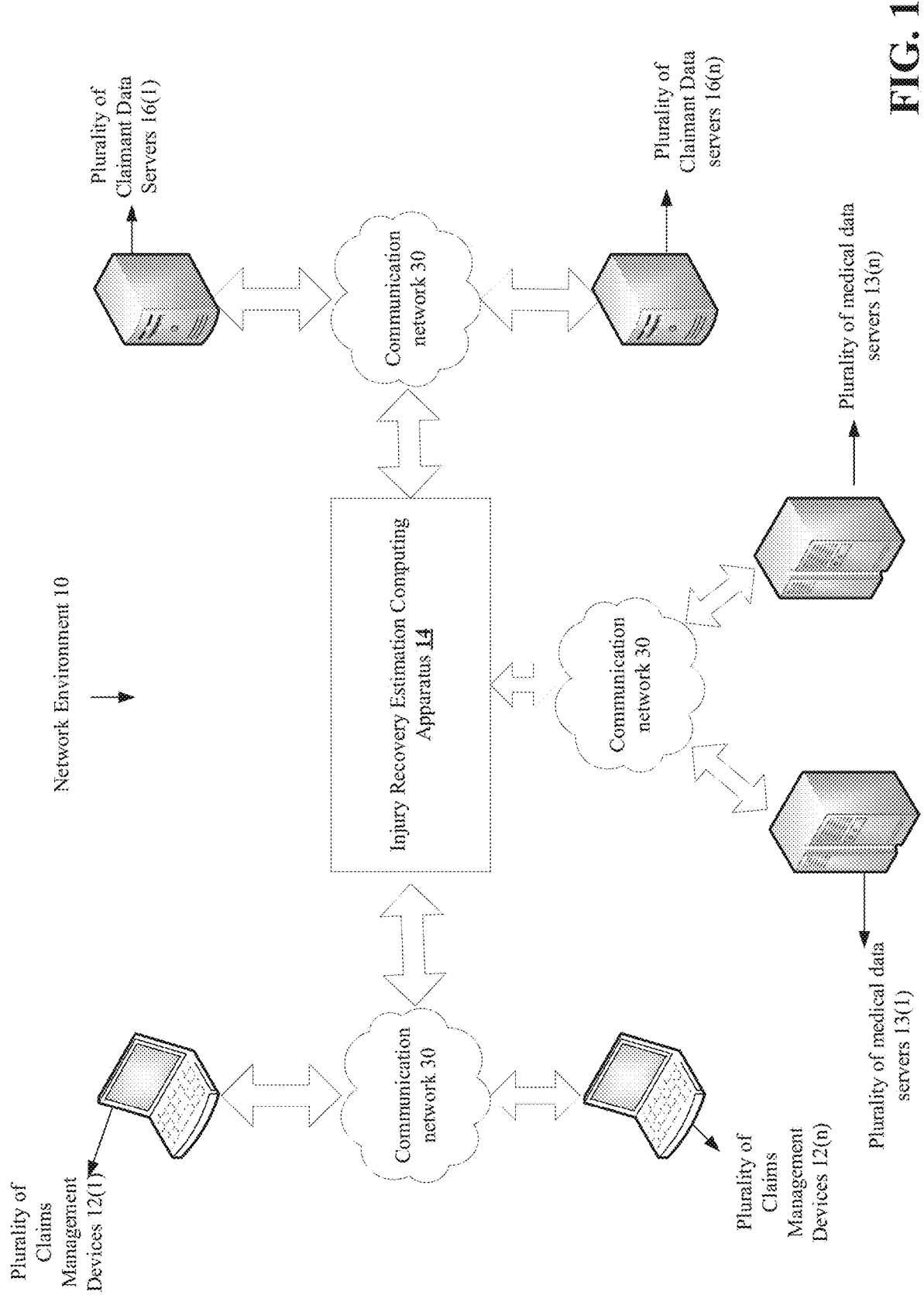
FIG. 1 is a block diagram of an environment with an example of a injury recovery estimation computing apparatus that accurately estimating injury recovery time data.
Figure 2:
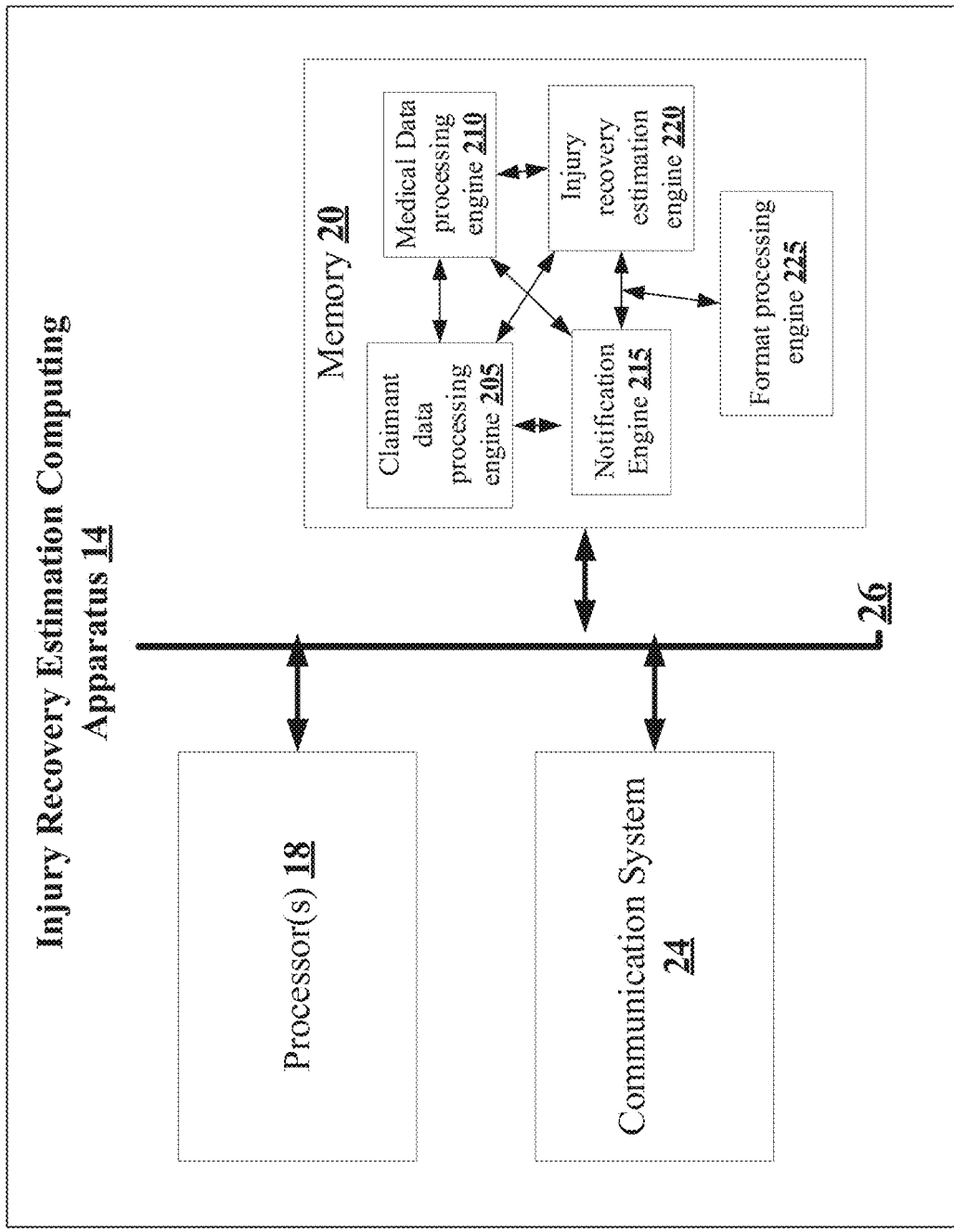
FIG. 2 is a block diagram of the example of the injury recovery estimation computing apparatus shown in FIG. 1.

Referring more specifically to FIGS. 1-2, the injury recovery estimation computing apparatus 14 is programmed to provide efficient methods to accurately predict injury recovery time data data; although the apparatus can perform other types and/or numbers of functions or other operations and this technology can be utilized with other types of claims. In this particular example, the injury recovery estimation computing apparatus 14 includes a processor 18, a memory 20, and a communication system 24 which are coupled together by a bus 26, although the injury recovery estimation computing apparatus 14 may comprise other types and/or numbers of physical and/or virtual systems, devices, components, and/or other elements in other configurations.

The processor 18 in the injury recovery estimation computing apparatus 14 may execute one or more programmed instructions stored in the memory 20 for accurately predicting injury recovery time data data as illustrated and described in the examples herein, although other types and/or numbers of functions and/or other operations can be performed. The processor 18 in the injury recovery estimation computing apparatus 14 may include one or more central processing units and/or general purpose processors with one or more processing cores, for example.

The memory 20 in the injury recovery estimation computing apparatus 14 stores the programmed instructions and other data for one or more aspects of the present technology as described and illustrated herein, although some or all of the programmed instructions could be stored and executed elsewhere. A variety of different types of memory storage devices, such as a random access memory (RAM) or a read only memory (ROM) in the system or a floppy disk, hard disk, CD ROM, DVD ROM, or other computer readable medium which is read from and written to by a magnetic, optical, or other reading and writing system that is coupled to the processor 18, can be used for the memory 20. Additionally, as illustrated in FIG. 2, memory 20 includes a claimant data processing engine 205, a medical data processing engine 210, a notification engine 215, an injury recovery estimation engine 220, and a format processing engine 225, although the memory 20 can include other types and/or amounts of modules, engines, or components to assist with accurate estimation of recovery time from an injury. In this example, the claimant data processing engine 205 assists with obtaining and processing of the claimant data from the plurality of claimant data servers 16(1)-16(n), although the claimant data processing engine 205 can be configured to perform other operations and/or functions. Next, the medical data processing engine 210 within the memory 20 assists with processing of the medical data associated with an insurance claimant or the demographic medical data obtained from the plurality of medical data servers 13(1)-13(n), although the medical data processing engine 210 can be configured to perform other types and/or numbers of functions. Next, the notification engine 215, in this example, is configured to assist the injury recovery estimation computing apparatus 14 with sending out notification to the plurality of claims management devices 12(1)-12(n) when the estimated injury recovery time is an outlier (indicating additional investigation is required) or when the estimated injury recovery time is determined, although the notification engine 215 can be configured to perform other types and/or numbers of operations. Furthermore, memory 20 includes an injury recovery estimation engine 220 that assists with determining the injury recovery time for all the injuries identified in the claimant data using the medical data, the claimant data, and the demographic data, although the injury recovery estimation engine 210 can be configured to perform other types and/or numbers of functions. Additionally, the format processing engine 225 in this example, assists with converting the data obtained in different formats to a standard or otherwise compatible format so that the injury recovery estimation computing apparatus 14 can accurately estimate the injury recovery time, although the format processing engine 225 can be configured to perform other types and/or numbers of operations.

The communication system 24 in the injury recovery estimation computing apparatus 14 operatively couples and communicates between one or more of the plurality of claims management devices 12(1)-12(n), one or more of the plurality of medical data servers 13(1)-13(n), one or more of the plurality of claimant data servers 16(1)-16(n), which are all coupled together by one or more of the communication networks 30, although other types and numbers of communication networks or systems with other types and numbers of connections and configurations to other devices and elements. By way of example only, the communication networks 30 can use TCP/IP over Ethernet and industry-standard protocols, including NFS, CIFS, SOAP, XML, LDAP, SCSI, and SNMP, although other types and numbers of communication networks, can be used. The communication networks 30 in this example may employ any suitable interface mechanisms and network communication technologies, including, for example, any local area network, any wide area network (e.g., Internet), teletraffic in any suitable form (e.g., voice, modem, and the like), Public Switched Telephone Network (PSTNs), Ethernet-based Packet Data Networks (PDNs), and any combinations thereof and the like.

In this particular example, each of the plurality of claims management devices 12(1)-12(n) may submit requests for predicting the injury recovery time data to the injury recovery estimation computing apparatus 14, although the requests can be obtained by the injury recovery estimation computing apparatus 14 in other manners and/or from other sources. Each of the plurality of claims management devices 12(1)-12(n) may include a processor, a memory, user input device, such as a keyboard, mouse, and/or interactive display screen by way of example only, a display device, and a communication interface, which are coupled together by a bus or other link, although each may have other types and/or numbers of other systems, devices, components, and/or other elements.

The plurality of medical data servers 13(1)-13(n) may store and provide medical data associated with other claimants, by way of example only, to the injury recovery estimation computing apparatus 14 via one or more of the communication networks 30, for example, although other types and/or numbers of storage media in other configurations could be used. In this particular example, each of the plurality of medical data servers 13(1)-13(n) may comprise various combinations and types of storage hardware and/or software and represent a system with multiple network server devices in a data storage pool, which may include internal or external networks. Various network processing applications, such as CIFS applications, NFS applications, HTTP Web Network server device applications, and/or FTP applications, may be operating on the plurality of medical data servers 13(1)-13(n) and may transmit data in response to requests from the injury recovery estimation computing apparatus 14. Each the plurality of medical data servers 13(1)-13(n) may include a processor, a memory, and a communication interface, which are coupled together by a bus or other link, although each may have other types and/or numbers of other systems, devices, components, and/or other elements.

The plurality of claimant data servers 16(1)-16(n) may store and provide claimant's medical data associated, by way of example only, to the injury recovery estimation computing apparatus 14 via one or more of the communication networks 30, for example, although other types and/or numbers of storage media in other configurations could be used. In this particular example, each of the plurality of claimant data servers 16(1)-16(n) may comprise various combinations and types of storage hardware and/or software and represent a system with multiple network server devices in a data storage pool, which may include internal or external networks. Various network processing applications, such as CIFS applications, NFS applications, HTTP Web Network server device applications, and/or FTP applications, may be operating on the plurality of claimant data servers 16(1)-16(n) and may transmit data in response to requests from the injury recovery estimation computing apparatus 14. Each the plurality of claimant data servers 16(1)-16(n) may include a processor, a memory, and a communication interface, which are coupled together by a bus or other link, although each may have other types and/or numbers of other systems, devices, components, and/or other elements.

Although the exemplary network environment 10 with the injury recovery estimation computing apparatus 14, the plurality of claims management devices 12(1)-12(n), the plurality of medical data servers 13(1)-13(n), the plurality of claimant data servers 16(1)-16(n), and the communication networks 30 are described and illustrated herein, other types and numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

Although the injury recovery estimation computing apparatus 14 is illustrated as single device, one or more actions of injury recovery estimation computing apparatus 14 may be distributed across one or more distinct network computing devices. Moreover, the injury recovery estimation computing apparatus 14 is not limited to a particular configuration. Thus, the injury recovery estimation computing apparatus 14 may contain a plurality of computing devices that operate using a master/slave approach, whereby one of the computing devices of the injury recovery estimation computing apparatus 14 operate to manage and/or otherwise coordinate operations of the other network computing devices. The injury recovery estimation computing apparatus 14 may operate as a plurality of computing devices within cluster architecture, a peer-to peer architecture, virtual machines, or within a cloud architecture.

Thus, the technology disclosed herein is not to be construed as being limited to a single environment and other configurations and architectures are also envisaged. For example, the plurality of claims management devices 12(1)-12(n), the plurality of medical data servers 13(1)-13(n), or the plurality of claimant data servers 16(1)-16(n) as depicted in FIG. 1 can operate within injury recovery estimation computing apparatus 14 rather than as a stand-alone server communicating with injury recovery estimation computing apparatus 14 via the communication network(s) 30.

While the injury recovery estimation computing apparatus 14 is illustrated in this example as including a single device, injury recovery estimation computing apparatus 14 in other examples can include a plurality of devices or blades each with one or more processors each processor with one or more processing cores that implement one or more steps of this technology. In these examples, one or more of the devices can have a dedicated communication interface or memory. Alternatively, one or more of the devices can utilize the memory, communication interface, or other hardware or software components of one or more other communicably coupled of the devices. Additionally, one or more of the devices that together comprise injury recovery estimation computing apparatus 14 in other examples can be standalone devices or integrated with one or more other devices or applications, such as one of the plurality of claims management devices 12(1)-12(n), plurality of medical data servers 13(1)-13(n), or the one of the plurality of claimant data servers 16(1)-16(n) or, the injury recovery estimation computing apparatus 14, or applications coupled to the communication network(s) 30, for example. Moreover, one or more of the devices of the injury recovery estimation computing apparatus 14 in these examples can be in a same or a different communication network 30 including one or more public, private, or cloud networks, for example.

Further, each of the systems of the examples may be conveniently implemented using one or more general purpose computer systems, microprocessors, digital signal processors, and micro-controllers, programmed according to the teachings of the examples, as described and illustrated herein, and as will be appreciated by those of ordinary skill in the art.

In addition, two or more computing systems or devices can be substituted for any one of the systems or devices in any example. Accordingly, principles and advantages of distributed processing, such as redundancy and replication also can be implemented, as desired, to increase the robustness and performance of the devices, apparatuses, and systems of the examples. The examples may also be implemented on computer system(s) that extend across any suitable network using any suitable interface mechanisms and traffic technologies, including by way of example only teletraffic in any suitable form (e.g., voice and modem), wireless traffic media, wireless traffic networks, cellular traffic networks, G3 traffic networks, Public Switched Telephone Network (PSTNs), Packet Data Networks (PDNs), the Internet, intranets, and combinations thereof.

The examples also may be embodied as a non-transitory computer readable medium having instructions stored thereon for one or more aspects of the present technology as described and illustrated by way of the examples herein, as described herein, which when executed by the processor, cause the processor to carry out the steps necessary to implement the methods of this technology as described and illustrated with the examples herein.

An example of a method for predicting the injury recovery time data will now be described with reference to FIGS.

Figure 3:
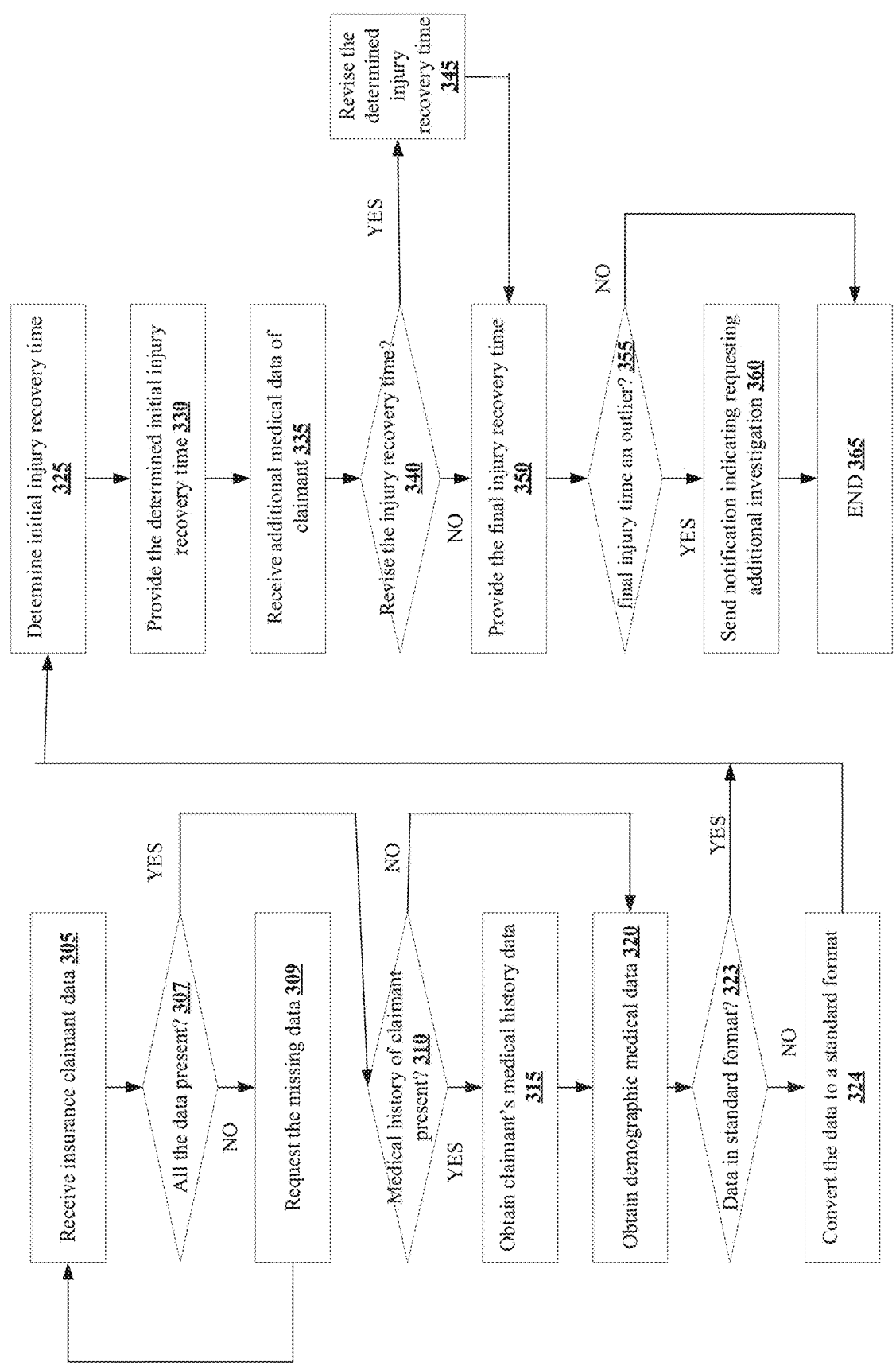
FIG. 3 is a flowchart of an example of a method for accurately estimating injury recovery time data.

1-4. In particular, referring to FIG. 3 the exemplary method begins at step 305 where the injury recovery estimation computing apparatus 14 receives insurance claimant data from one of a plurality of claims management devices 12(1)-12(n), although the injury recovery estimation computing apparatus 14 can receive other types of data. In this example, the claimant data can include data associated with claimant's one or more current injuries, medical history, unique identification number associated with the claimant, and/or other claim related data, although the claimant data can include other types of data and/or other information. Alternatively in another example, the injury recovery estimation computing apparatus 14 can provide a graphical user interface via which the requesting one of the plurality of claims management devices 12(1)-12(n) can access and submit the insurance claimant data.

In step 307, the injury recovery estimation computing apparatus 14 determines when the received insurance claimant data includes the data necessary to estimate the injury recovery time, such as the list of one or more injuries including descriptive data related to each of the one or more injuries, and the unique identification number, although other types and/or amounts of data can be required to estimate the injury recovery time. In this example, the injury recovery estimation computing apparatus 14 parses the received claimant data to identify keywords related to necessary data to extract, such as terms related to different injuries, descriptions of different injuries, and the identification numbers to determine if there is data available needed to estimate the injury recovery time, although other techniques can be used to make the determination. Accordingly, when the injury recovery estimation computing apparatus 14 determines that the data necessary to estimate the injury recovery time is present, then the Yes branch is taken to step 310 which will be further illustrated below. However, when the injury recovery estimation computing apparatus 14 determines that the data necessary to estimate the injury recovery time is not present in the received insurance claimant data, then the No branch is taken to step 309.

In step 309, the injury recovery estimation computing apparatus 14 sends a request for specific claimant data that is not present in the initially received claimant data to the requesting one of the plurality of claims management devices 12(1)-12(n) and the exemplary flow proceeds to step 305 to receive the requested data. In this example, steps 307 to 309 would iteratively repeat until the injury recovery estimation computing apparatus 14 has all the data required to accurately determine the estimated injury recovery time.

In step 310, the injury recovery estimation computing apparatus 14 determines when there is medical history data associated with the claimant by searching medical history data stored in one of the plurality of claimant data servers 16(1)-16(n) using the unique identification number; although other techniques can be used to make the determination. When the injury recovery estimation computing apparatus 14 determines there is medical history data associated with the claimant, then the Yes branch is taken to step 315.

In step 315, the injury recovery estimation computing apparatus 14 obtains claimant's medical history data from one or more of the plurality of claimant data servers 16(1)-16(n) using the unique identification number associated with the claimant, although the claimant's medical history data can be obtained in other manners and from other locations. In this example, the claimant's medical history data may include date, time and type of prior injuries and amount of time taken to recover from the prior injuries, although the claimant's medical history data can include other types and/or amounts of information. By considering the amount of time taken to recover from prior injuries, the disclosed technology might estimate a higher injury recovery time data for a claimant which otherwise could be classified as an outlier which will be further illustrated below in step 355.

If back in step 310, the injury recovery estimation computing apparatus 14 determines there is not sufficient medical history data associated with the claimant, then the No branch is taken to step 320. In step 320, the injury recovery estimation computing apparatus 14 obtains demographic medical data associated with other claimants having the same injuries in the received insurance claimant data from one of the plurality of medical data servers 13(1)-13(n), although the injury recovery estimation computing apparatus 14 can obtain other types of data from other locations. In this example, the demographic medical data includes recovery time data of other claimants having same injuries within the same age group and gender classification of the claimant, although the demographic medical data can include other types and/or amounts of information. Alternatively, the injury recovery estimation computing apparatus 14 can obtain demographic medical data associated with other claimants having same injuries within the same age group but a different gender classification of the claimant. In yet another example, the injury recovery estimation computing apparatus 14 can obtain demographic medical data associated with other claimants having same injuries with an age that falls within a range of the insurance claimant's age with either same gender or difference gender classification.

In step 323, the injury recovery estimation computing apparatus 14 determines when the obtained medical history data, the obtained demographic data, and the received insurance claimant data is in a standard or other compatible format for determining the estimated recovery time data. Accordingly, when the injury recovery estimation computing apparatus 14 determines that the obtained history data, the obtained demographic data, and the received insurance claimant data are in a standard or otherwise compatible format for processing, then the Yes branch is taken to step 325 which will be further illustrated below. However, when the injury recovery estimation computing apparatus 14 determines that the obtained history data, the obtained demographic data, and the received insurance claimant data is not in a standard or otherwise compatible format, then the No branch is taken to step 324.

In step 324, the injury recovery estimation computing apparatus 14 converts the obtained medical history data, the obtained demographic data, and the received insurance claimant data into a standard or otherwise compatible format. By converting the obtained data into a standard or otherwise compatible format, the disclosed technology is able to process data obtained in different formats to accurately estimate the injury recovery time.

In step 325, the injury recovery estimation computing apparatus 14 determines initial injury recovery time data for the received claimant data based on the obtained claimant's medical history, the one or more injuries listed in the insurance claimant data, and the obtained demographic medical data, although the injury recovery estimation computing apparatus 14 can determine injury recovery time data using other parameters and techniques. In this example, the injury recovery estimation computing apparatus 14 uses one or more programmed estimation rules stored within the memory 20 to identify statistical correspondence and correlate the type of injury, gender, and the age of the claimant to the obtained demographic medical data (stored within a table) to estimate the initial injury recovery time data. By way of example, if the claimant is a male of age twenty five years and has a fractured right elbow, then the injury recovery estimation computing apparatus 14 correlates the time taken to recover from an injury for a male of age twenty five years and with fractured right elbow from the obtained demographic medical data. Additionally, the injury recovery estimation computing apparatus 14 also considers the claimant's medical history while determine the injury recovery time data. By way of example, if the claimant is a male of age twenty five years, has a fractured right elbow, and has a medical history of osteoporosis, then the injury recovery estimation computing apparatus 14 correlates the time taken to recover from an injury for a male of age twenty five years with fractured right elbow having a medical history of osteoporosis from the obtained demographic medical data. Accordingly, one of the programmed estimation rules can include correlating received claimant's data with the obtained demographic medical data within the same age, gender, and injury category of the insurance claimant. However back in step 310, when the injury recovery estimation computing apparatus 14 determines that there is no medical history associated with the claimant, the injury recovery estimation computing apparatus 14 determines the initial injury recovery time only based on the obtained demographic medical data as illustrated above.

Alternatively in another example, the injury recovery estimation computing apparatus 14 determines initial injury recovery time data for the received claimant data by correlating at least demographic medical data comprising prior estimated injury recovery time data associated with different prior claimant's ages, genders, and injuries based on one or more programmed estimation rules configured to identify statistical correspondence between different combinations of the ages, the genders, and the injuries in the demographic medical data and the claimant medical data comprising at least the current claimant's age, gender, and at least one injury. By way of example, the injury recovery estimation computing apparatus 14 can identify statistical correspondence and correlate a male of forty years of age with broken arm with a female of age forty one with and broken arm. Accordingly, one of the programmed estimation rules can include allowing correlation between data of different gender classification within a range of the age group but with the same injuries. Additionally, the injury recovery estimation computing apparatus 14 can also adjust the range of the age group based on the claimant's age. For example, one of the programmed estimation rules is to allow the smaller age range such as five to ten years or ten to fifteen years for younger claimants but have a larger age ranger such as forty to fifty or fifty to sixty for older claimants.

In step 330, the injury recovery estimation computing apparatus 14 provides the determined initial injury recovery time back to the requesting one of the plurality of claims management devices 12(1)-12(n), although the initial injury recovery time can be provided to other devices.

Next in step 335, the injury recovery estimation computing apparatus 14 receives additional medical data associated with the claimant from one of the plurality of claims management devices 12(1)-12(n), although the injury recovery estimation computing apparatus 14 can receive other types of data from other devices. By way of example, additional medical data can include medication and/or treatment prescribed for the claimant's injury, although the additional medical data can include other types and/or amounts of information. Alternatively, the injury recovery estimation computing apparatus 14 can receive the additional medical data via a graphical user interface that is generated by the injury recovery estimation computing apparatus 14 and provided to the requesting one of the plurality of claims management devices 12(1)-12(n).

In step 340, the injury recovery estimation computing apparatus 14 determines when the initial injury time determined in step 325 is required to be revised based on the additional medical data. In this example, the injury recovery estimation computing apparatus 14 again correlates the claimant data received in step 305, the obtained claimant's medical history data in step 310, and the additional medical data in step 335 to the demographic data and identifies a new injury recovery time data. The injury recovery estimation computing apparatus 14 then compares the initial injury recovery time data with the new injury recovery time data and if there is a deviation between the two, then the injury recovery estimation computing apparatus 14 determines that the injury recovery time data is required to be revised. Accordingly, when the injury recovery estimation computing apparatus 14 determines that the injury time is required to be revised, then the Yes branch is taken to step 335.

In step 345, the injury recovery estimation computing apparatus 14 revises the initial injury recovery time data with the new injury recovery time data and the exemplary flow proceeds to step 350.

Figure 4:
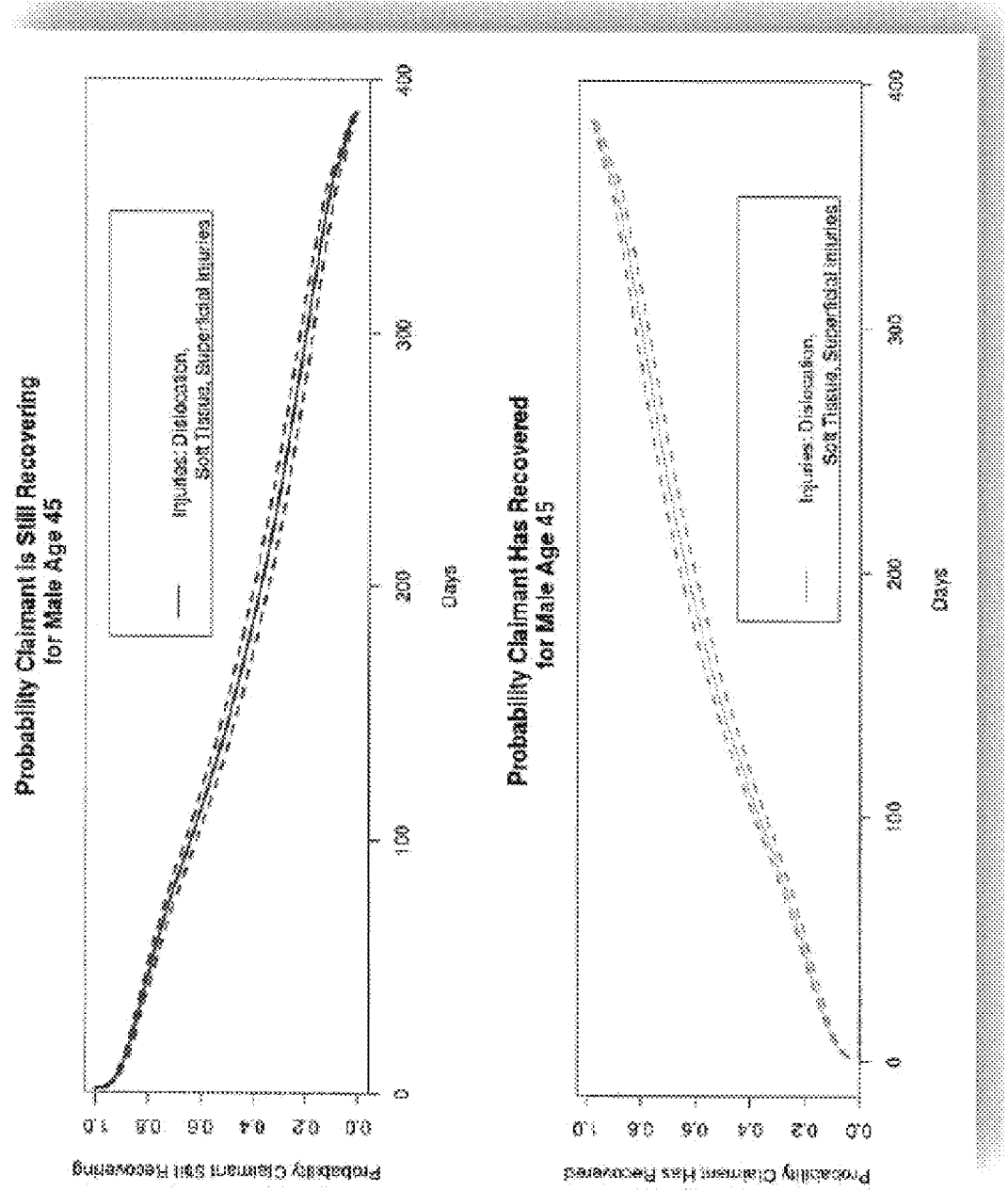
FIG. 4 is an exemplary graph illustrating the injury recovery time of the claimant.

However, if back in step 340 the injury recovery estimation computing apparatus 14 determines that the injury recovery time data is not required to be revised, then the No branch is taken to step 350. In step 350, the injury recovery estimation computing apparatus 14 provides either the new injury recovery time data or the initial injury recovery time data to the requesting one of the plurality of claims management devices 12(1)-12(n). Additionally in this example, the injury recovery estimation computing apparatus 14 can provide a graphical representation of the injury recovery time data and the likelihood of recovery on a graphical user interface as illustrated in FIG. 4. Alternatively, the injury recovery estimation computing apparatus 14 can provide the injury recovery time data to the requesting one of the plurality of claims management devices 12(1)-12(n) by displaying on the graphical user interface in real time.

In step 355, the injury recovery estimation computing apparatus 14 determines when the final injury recovery time is above a threshold percentage of the stored injury recovery time data present within the demographic medical data obtained in step 320. By way of example, if the final injury recovery time is fifteen days and if the stored injury recovery time is ten days and the threshold percentage is ten percent; then the injury recovery estimation computing apparatus 14 determines that the final injury recovery time is an outlier because the final injury recovery time (fifteen days) is above stored injury recovery time (ten days) plus threshold percentage (ten percent) of the stored injury recovery time, i.e, ten days plus ten percent of ten days, which is equal to eleven days. Accordingly, when the injury estimation computing apparatus 14 determines that the final injury recovery time is not an outlier, then the No branch is taken to step 365 where the exemplary method ends. However, when the injury estimation computing apparatus 14 determines that the final injury recovery time is an outlier, then the Yes branch is taken to step 360.

In step 360, the injury recovery estimation computing apparatus 14 sends out a notification to the requesting one of the plurality of claims management devices 12(1)-12(n) indicating that additional investigation is required to be performed as the received claimant data could be a fraudulent claimant data. Additionally in this example, injury recovery estimation computing apparatus 14 can provide the notification via a graphical user interface Alternatively, in another example, the injury recovery estimation computing apparatus 14 can determine when the final injury recovery time is the lowest when compared to the demographic medical data obtained in step 320 using the technique illustrated above in step 325. By way of example, the injury recovery estimation computing apparatus 14 sequentially compares the final injury recovery time that was provided in step 350 against each of the injury recovery time present in the obtained demographic data for the same age, gender, and injury diagnosed for the claimant and determines if the final injury recovery time is the lowest. Accordingly, when the injury recovery estimation computing apparatus 14 determines that the final injury recovery time is the lowest, then the exemplary method ends. However, when the injury recovery estimation computing apparatus 14 determines that the final injury recovery time is not the lowest, then the injury recovery estimation computing apparatus 14 can provide a notification to the requesting one of the plurality of claims management devices 12(1)-12(n) to indicate availability other treatments available to reduce the final injury recovery time.

Accordingly, this technology provides methods, non-transitory computer readable medium, and apparatuses that accurately automates estimating injury recovery time. By using the techniques illustrated above, the disclosed technology provides a technological solution by considering large amounts of medical data associated with the claimant and the demographic data in different formats while estimating the injury recovery time. Additionally, the disclosed technology also identifies any possible outliers with respect to the amount of time taken to recover from an injury and sends out a notification for further investigation. By doing so, the disclosed technology is able to prevent fraudulent insurance claims from being processed and therefore is closely tied to the practical application of estimating injury recovery time.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method comprising:
   extracting, by a computing device, claimant medical data comprising at least a current claimant's age, gender, and at least one injury from an electronic claims document;
   determining, by the computing device, estimated injury recovery time data by correlating at least demographic medical data comprising prior estimated injury recovery time data associated with different prior claimant's ages, genders, and injuries based on one or more programmed estimation rules configured to identify statistical correspondence between different combinations of the ages, the genders, and the injuries in the demographic medical data and the claimant medical data comprising at least the current claimant's age, gender, and at least one injury;
   updating, by the computing device, the determined estimated injury recovery time data based on at least identified and obtained medical treatment data and prescription medication data associated with the current claimant's at least one injury;
   providing, by the computing device, the updated estimated injury recovery time data via a plurality of graphical user interfaces of requesting claim management devices; and
   transmitting, by the computing device, a plurality of notifications to the requesting claim management devices only when the estimated injury recovery time is an outlier or when the estimated injury recovery time is determined.

2. The method as set forth in claim 1 further comprising:
   comparing, by the computing device, the updated estimated injury recovery time data against stored threshold injury recovery time data from a table correlated to the claimant's at least one injury;
   determining, by the computing device, when the updated estimated injury recovery time data is a threshold percentage above the stored estimated injury recovery time data; and
   providing, by the computing device, an outlier notification via the graphical user interface to the requesting claim management device when the updated injury recovery time data is determined to be above the threshold percentage.

3. The method as set forth in claim 1 further comprising, determining, by the computing device, when claimant medical data includes data necessary to determine the estimated injury recovery time data.

4. The method as set forth in claim 3 further comprising, sending, by the computing device, a specific request for missing data when the data necessary to determine the estimated injury recovery time data is determined to be absent.

5. The method as set forth in claim 1 wherein the estimated injury recovery time data is determined based on claimant's medical history data comprising an amount of time taken to recover from one or more prior injuries.

6. The method as set forth in claim 1 wherein the claimant medical data is extracted by identifying one or more keywords.

7. A non-transitory computer readable medium having stored thereon instructions comprising executable code, which when executed by at least one processor, cause the processor to:
   extract claimant medical data comprising at least a current claimant's age, gender, and at least one injury from an electronic claims document;
   determine estimated injury recovery time data by correlating at least demographic medical data comprising prior estimated injury recovery time data associated with different prior claimant's ages, genders, and injuries based on one or more programmed estimation rules configured to identify statistical correspondence between different combinations of the ages, the genders, and the injuries in the demographic medical data and the claimant medical data comprising at least the current claimant's age, gender, and at least one injury;
   update the determined estimated injury recovery time data based on at least identified and obtained medical treatment data and prescription medication data associated with the current claimant's at least one injury; provide the updated estimated injury recovery time data via a plurality of graphical user interface interfaces of requesting claim management devices; and transmit a plurality of notifications to the requesting claim management devices only when the estimated injury recovery time is an outlier or when the estimated injury recovery time is determined.

8. The medium as set forth in claim 7 further comprising:

comparing the updated estimated injury recovery time data against stored threshold injury recovery time data from a table correlated to the claimant's at least one injury;

determining when the updated estimated injury recovery time data is a threshold percentage above the stored estimated injury recovery time data; and providing an outlier notification via the graphical user interface to the requesting claim management device when the updated injury recovery time data is determined to be above the threshold percentage.

9. The medium as set forth in claim 7 further comprising, determining when claimant medical data includes data necessary to determine the estimated injury recovery time data.

10. The medium as set forth in claim 9 further comprising, sending a specific request for missing data when the data necessary to determine the estimated injury recovery time data is determined to be absent.

11. The medium as set forth in claim 7 wherein the estimated injury recovery time data is determined based on claimant's medical history data comprising an amount of time taken to recover from one or more prior injuries.

12. The medium as set forth in claim 7 wherein the claimant medical data is extracted by identifying one or more keywords.

13. An injury recovery estimation computing apparatus comprising:
   a processor; and
   a memory coupled to the processor which is configured to be capable of executing programmed instructions comprising and stored in the memory to:
   extract claimant medical data comprising at least a current claimant's age, gender, and at least one injury from an electronic claims document;
   determine estimated injury recovery time data by correlating at least demographic medical data comprising prior estimated injury recovery time data associated with different prior claimant's ages, genders, and injuries based on one or more programmed estimation rules configured to identify statistical correspondence between different combinations of the ages, the genders, and the injuries in the demographic medical data and the claimant medical data comprising at least the current claimant's age, gender, and at least one injury;
   update the determined estimated injury recovery time data based on at least identified and obtained medical treatment data and prescription medication data associated with the current claimant's at least one injury; provide the updated estimated injury recovery time data via a plurality of graphical user interfaces of requesting claim management devices; and
   transmit a plurality of notifications to the requesting claim management devices only when the estimated injury recovery time is an outlier or when the estimated injury recovery time is determined.

14. The apparatus as set forth in claim 13 wherein the processor is further configured to be capable of executing the stored programmed instructions to:
   compare the updated estimated injury recovery time data against stored threshold injury recovery time data from a table correlated to the claimant's at least one injury;
   determine when the updated estimated injury recovery time data is a threshold percentage above the stored estimated injury recovery time data; and
   provide an outlier notification via the graphical user interface to the requesting claim management device when the updated injury recovery time data is determined to be above the threshold percentage.

15. The apparatus as set forth in claim 13 wherein the processor is further configured to be capable of executing the stored programmed instructions to determine when claimant medical data includes data necessary to determine the estimated injury recovery time data.

16. The apparatus as set forth in claim 15 wherein the processor is further configured to be capable of executing the stored programmed instructions to send a specific request for missing data when the data necessary to determine the estimated injury recovery time data is determined to be absent.

17. The apparatus as set forth in claim 13 wherein the estimated injury recovery time data is determined based on claimant's medical history data comprising an amount of time taken to recover from one or more prior injuries.

18. The apparatus as set forth in claim 13 wherein the claimant medical data is extracted by identifying one or more keywords.

* * * * *